United States Patent [19]

Ciaperoni et al.

[11] 4,279,652
[45] Jul. 21, 1981

[54] SELF-EXTINGUISHING POLYMERS

[75] Inventors: Aldemaro Ciaperoni, Bollate-Milan; Antonino Cucinella, Como, both of Italy

[73] Assignee: Sniaviscosa Societa Nazionale Industria Applicazioni Viscosa, S.p.A., Milan, Italy

[21] Appl. No.: 833,554

[22] Filed: Sep. 15, 1977

[30] Foreign Application Priority Data

Sep. 15, 1976 [IT] Italy ............................ 27198 A/76
Jul. 20, 1977 [IT] Italy ............................ 25902 A/77

[51] Int. Cl.³ .......................... C08K 5/16; C08K 5/34
[52] U.S. Cl. ................................ 106/18.21; 252/608; 252/609; 260/45.8 NT; 260/45.9 R
[58] Field of Search ............... 260/45.8 NT, 45.8 NE; 8/190; 427/390 D; 544/192; 106/165, 168, 18.14, 18.21

[56] References Cited

U.S. PATENT DOCUMENTS

| | | | |
|---|---|---|---|
| 2,507,700 | 5/1950 | Emerson et al. ............. | 544/196 |
| 2,544,706 | 3/1951 | Marlowan ..................... | 106/15 FP |
| 2,603,614 | 7/1952 | Nielsen et al. ............... | 260/30.2 |
| 2,768,167 | 10/1956 | Marzluff et al. ............. | 544/192 |
| 3,645,936 | 2/1972 | Gardner ........................ | 8/190 |
| 3,660,344 | 5/1972 | Michael et al. .............. | 260/45.8 NT |
| 3,744,970 | 7/1973 | Swidler et al. ............... | 8/190 |
| 3,787,407 | 1/1974 | Hendricks .................... | 106/15 FP |
| 3,793,289 | 2/1974 | Koch et al. .................. | 260/45.8 NT |
| 3,849,409 | 11/1974 | Weil .............................. | 8/190 |
| 3,877,974 | 4/1975 | Mischutin .................... | 427/390 D |
| 3,947,276 | 3/1976 | Siclari et al. ................. | 106/15 FP |
| 3,955,032 | 5/1976 | Mischutin et al. .......... | 427/390 D |
| 3,974,251 | 8/1976 | Cremer et al. ............... | 106/15 FP |
| 3,980,616 | 9/1976 | Kimura et al. ............... | 260/45.8 NT |
| 4,001,177 | 1/1977 | Tsutsumi et al. ............ | 260/45.8 NT |
| 4,003,861 | 1/1977 | Savides et al. ............... | 260/45.8 NT |
| 4,028,333 | 6/1977 | Lindvay ........................ | 260/45.8 NT |
| 4,055,720 | 10/1977 | Chance et al. ............... | 8/190 |
| 4,096,206 | 6/1978 | Boyer ........................... | 260/45.8 NT |
| 4,122,269 | 10/1978 | Chono et al. ................ | 260/45.8 NT |

OTHER PUBLICATIONS

Melamine Bulletin, Reichhold Chemicals, Inc., 1965.
Noller, "Chemistry of Organic Compounds", 1957, pp. 234 and 236.
Smolin et al., s–Triazines and Derivatives, 1959, pp. 328 and 329.

*Primary Examiner*—Hosea E. Taylor
*Assistant Examiner*—R. A. White
*Attorney, Agent, or Firm*—Burgess, Ryan and Wayne

[57] ABSTRACT

A new composition is described comprising a synthetic, artificial or natural polymer and a flameproofing additive imparting self-extinguishing properties to the composition and to the articles, such as moulded, spun or woven articles, made therefrom, said additive being the product of the reaction of melamine with acidic compounds, such as organic acids or anhydrides and inorganic acids. The process for making said additive by said reaction, preferably in the presence of water, is also described. The said composition may be made by introducing said additive in any manufacturing stage, viz. to the monomers (if the polymer is a synthetic one), to the molten polymer, to polymer solutions such as viscose dope, to polymer chips during extrusion, or to finished products e.g. by applying a finish to fabrics.

6 Claims, No Drawings

SELF-EXTINGUISHING POLYMERS

BACKGROUND OF THE INVENTION (a) Field of the Invention

The present invention refers to a new composition based on a natural, artificial and/or synthetic polymer, having self-extinguishing properties. In the description of the present invention, "synthetic polymer" means in particular a polyamide, a copolyamide, a polyester, or a copolyester; "artificial polymer" means in particular regenerated cellulose materials; and "natural polymer" means in particular cotton.

The present invention further refers to a process for rendering a composition based on said polymer or polymers, self-extinguishing, by adding a particular self-extinguishing additive, which will be better specified hereinafter, to the polymer itself, or, in the case of synthetic polymers, said additive may be added during the polymerization or before their transformation into formed materials. Further objects of the present invention will be indicated hereinafter.

(b) The prior art

It has been known for many years that the polymers of natural, artificial or synthetic origin constitute a danger because of their inflammability. This danger is particularly intensified in the case of textile materials, which contribute to a high percentage of accidents due to ignition of wearing apparel or textile products for furniture. The textile materials in regard to which the inflammability problem is particularly felt, are those derived from cellulosic fibres (rayon and/or cotton), synthetic fibres (such as polyamide, polyester) and also mixtures of cellulosic with synthetic fibres.

In general, in order to render a product self-extinguishing there exist mainly the following techniques:

(1) to use in the polymerization comonomers having self-extinguishing properties; and/or
(2) to add substances having self-extinguishing properties to the polymers by means of extrusion operations in an extruder; and/or
(3) to apply finishes containing self-extinguishing substances onto articles, e.g. fabrics, films, curtains, etc.

In order that one of methods (1) or (2) may be successful, it is necessary that the self-extinguishing agents employed should not produce or promote degradation reactions or other harmful reactions during the polymerization or whenever they are added. For instance, in the case of the polyamides, some types of products which impart self-extinguishing properties and which are used successfully for other classes of polymers, such as polyethyleneterephthalate, have proved to be unsuitable. Among these may be cited the halogenated compounds, in particular organic brominated or chlorinated compounds, which in the case of the polyamides cause a strong degradation of the polymer without significantly delaying the propagation of the flame.

Also certain phosphorated additives, which are notoriously self-extinguishing, especially in the presence of nitrogen containing substances, exert their self-extinguishing activity on the polyamides only when they are added in such high amounts as to affect negatively the peculiar characteristics of the polymer, such as spinnability, mechanical properties, color, etc.

Finally, certain substances containing nitrogen and sulphur, such as thiourea, ammonium sulphamate, thiocyanates, are not adapted for the polyamides when employed as comonomers or added by mixing them with the polymer in the molten state since they promote viscosity degradation and colour alteration of the polymer. For this reason such products or the polymers derived therefrom (urea, thiourea with formaldehyde and/or with melamine) are employed as self-extinguishing components only according to method (3), for polyamidic textile articles. Melamine, which confers to the polyamide a certain degree of flame retardant properties, has the disadvantage that it is not soluble in polycapronamide even at a concentration of 0.5%. Actually, the requirement of the homogeneity of the flame retardant agent in the polymer is fundamental, if the polymer is intended to be used as a fibre.

Therefore it is natural that when method (1) or (2) cannot be used to impart properties of resistance to the flame, it becomes necessary to resort to method (3), which consists in the application of self-extinguishing finishes. Such method further is the only one available for imparting self-extinguishing properties to certain products of cellulosic origin, such as cotton products.

It is also known that mixtures of fibres of cellulosic origin with thermoplastic fibres (polyester, polyamide fibers), are not self-extinguishing even if one fibre component has been treated with a self-extinguishing additive. Therefore for such mixtures it is advantageous to effect finishing treatments with additives that are effective to impart self-extinguishing properties both to the cellulose and to the thermoplastic fibre. In these cases however, the choice of the additive or additives is a difficult one because their activity, understood as the capability to impart self-extinguishing properties, is not the same for different materials.

A suitable solution for rendering a synthetic polymer (based on a polyamide or a polyester) self-extinguishing, when it is desired to employ self-extinguishing additives to be added to the molten polymer, consists in finding substances that will not cause undesirable thermodegradation of the polymer and will not negatively interfere with its colour and/or its physico-chemical and mechanical characteristics. Because of the many negative factors hereinbefore mentioned, the production of flame retarded or self-extinguishing polymers of the classes mentioned (polyamides and/or polyesters) by the addition of self-extinguishing compounds to the molten polymer and/or by copolymerization with self-extinguishing monomers, has remained a problem to the present time.

SUMMARY OF THE INVENTION

The Applicants have now surprisingly found an additive which is particularly effective with regard to the combustion of said polymers; this product does not give rise to thermodegradative reactions and/or to irreversible alterations of the polymer to which it is added either during addition in an extruder or during thermoforming or even during polymerization (in the case of synthetic polymers). Said additive includes one or more products derived from the transformation of melamine, preferably in the presence of water, in an acid medium: said acidity may be provided by inorganic acids and/or anhydrides or by organic acids and/or corresponding anydrides or even by mixtures of organic and/or inorganic compounds of an acid character.

One object of the present invention is, therefore, to provide compositions based on a synthetic polymer, in particular a polyamide, a copolyamide, a polyester, or a copolyester, an artificial polymer in particular regenerated cellulose materials, or a natural polymer such as cotton, having self-extinguishing properties, characterized by the fact that they contain as a self-extinguishing additive, one or more products (A) derived from the transformation of melamine, preferably in the presence of water, and of at least a compound having an acid character chosen from the group consisting of an organic acid, an anhydride of an organic acid and an inorganic acid, wherein in the case that polyamide are treated, said product (A) may be further modified with caprolactam.

It is also to be understood that it is possible to employ as an acid medium, according to the invention, a mixture comprising one or more organic acids and/or inorganic acids in the presence or in the absence of one or more organic anhydrides, any combination between organic acids, inorganic acids and/or organic anhydrides being possible.

As an organic acid, formic, acetic or butyric acid is preferably employed; as anhydride of an organic acid, acetic, propionic, butyric or phthalic anhydride is preferably employed; and as an inorganic acid, sulphuric or phosphoric acid is preferably employed.

Product (A) may be added, in the case of synthetic polymers, for instance:

(1) by addition during the polymerization to monomers which form polyamides and/or copolyamides, polyesters and/or copolyesters;

(2) by addition in an extruder during the extrusion operation; the granules containing the additive may be used to obtain moulded bodies or may be used for melt spinning in order to obtain fibres and therefore textile manufacts which are self-extinguishing;

(3) by application of finishes essentially comprising an aqueous suspension and containing a binder capable of binding product (A) onto the fabric under heating.

In the case of regenerated cellulose materials, such as rayon, product (A) may be directly added to the viscose and subsequently precipitated in the coagulating bath (whereby product (A) remains incorporated in the cellulosic material) or may be applied by a finishing operation to the cellulosic fabric, analogously to what has been described for synthetic polymers under (3).

Further, in the case of fabrics comprising polyester/cotton mixtures, with different cotton percentages, or in the case of cotton alone, said fabrics may be rendered self-extinguishing with a suitable finishing operation as previously described under (3) for synthetic polymers.

Product (A) is preferably present in the polymeric composition in amounts from 0.5% to 30% inclusive, more preferably from 2% to 15% inclusive; said percentages being by weight with respect to the weight of the polymer.

In the preparation of the self-extinguishing additive (product A), the molar ratio of melamine to anhydride and/or to acid may vary widely; at any rate, it is preferred to operate with ratios from 4 to 0.1, preferably from 2 to 0.5.

According to the present invention, the transformation of the melamine in an aqueous-acid medium may occur under conditions known in the art for this type of reaction. The temperature may vary from 100° to more than 300° C., provided that the reaction vessel is capable of withstanding the autogenous pressure. Preferably, in order to take advantage of an appreciable reaction speed, the temperature should be above a lower limit of at least 130° C., or preferably between 150° C. and 180° C.

The product (A), which has self-extinguishing properties, obtained by the present invention, is constituted by carbon, hydrogen, nitrogen and oxygen. In particular, the carbon content is comprised in the range 25–60%, the nitrogen content is comprised between 3% and 60%, the rest being hydrogen and oxygen, the carbon content being more often 25–33%.

Additive (A) is a product which has shown a considerable versatility, inasmuch as it is effective both for synthetic polymeric materials, in particular those having amidic functional groups (e.g. polycaprolactam and hexamethylenediamine polyadipate), and for cellulosic materials (cotton and rayon) and/or textile mixtures rayon-polyester or cotton-polyester. Sometimes the additives of the art, which impart self-extinguishing properties to cellulosic fabrics, are not equally effective for the materials obtained from synthetic fibres or the additive itself has such a chemical structure and thermal stability that it must be employed only in finishes.

On the contrary, the additive of the present invention is possessed of other advantages, besides that of imparting self-extinguishing properties. In particular said additive exhibits the following properties:

(a) it is only slightly soluble in hot water (solubility less than 1 gr/lt), whereby the articles containing product (A) can maintain their self-extinguishing properties even after contact with water;

(b) it has very high melting and/or degradation temperatures (above 300° C.) and therefore it is possessed of a considerable thermal stability under the normal conditions of extrusion, moulding, polymerization, spinning of the materials for which it is intended;

(c) it disperses homogeneously in the polyamides up to substantial concentrations, e.g. greater than 10% by weight with respect to the polyamide.

A further object of the present invention is to provide a process for the preparation of the compositions based on synthetic, artificial or natural polymers, having self-extinguishing properties. Said process is characterized in that product (A) is added in an amount from 0.5% to 30%, preferably from 2% to 15%, inclusive (by weight), to the polymer, or, in the polymerization stage, to the monomers from which the polymer derives. More particularly said product (A) may, for instance, be added to and mixed with the polymer in an extruder in the extrusion operation or by application of a finish essentially constituted by an aqueous suspension and containing a binder capable of binding the product (A) onto the fabric by heat, or even may be added to the melt under stirring during the polymerization of the monomer or monomers which form the synthetic polymers such as polyamides, copolyamides, polyesters and copolyesters.

The self-extinguishing polymeric compositions which are an object of the present invention, are particularly adapted for uses as textile fibres (including non-woven fabrics), films, and articles extruded or formed in any way. Such fibres, films, articles, and the like containing the additive (product A) according to the invention, are also an object of the present invention.

Other compounds which may be optionally added together with product (A), are products which are known to be effective against thermo-oxidative degradations and are therefore effective in maintaining the white colour of the polymers, in particular in the case of polyamides. A chain extender, such as diphenylcarbonate, may also be added in amounts up to 0.5% by weight with respect to the polyamide; this product is effective against any possible decrease in the viscosity due to the flame retardant component, when this is added in substantial amounts, e.g. more than 10% by weight with respect to the polyamide.

The tests which have been carried out to determine the effectiveness of product (A) in imparting self-extinguishing properties, according to the invention, are known by the denominations: DOC FF 3-71 (standard for night pajamas for children, size 0-6); limiting oxygen index (L.O.I.) which indicates the minimum oxygen concentration necessary for combustion; U.L. (Underwriter's Laboratory) bulletin 94; ISO-TC 92 DOC 382 of the "Radiant Panel" (generally employed for wall coverings, ceilings, flooring, carpets). Finally, an empirical but highly significant test which permits evaluating the degree of the self-extinguishing properties on small amounts of thermoplastic polymer (e.g. polyamides), consists in determining the number of ignitions required for the complete combustion of a twine constituted by a plurality of monofilaments of a given length, as will be described in the following examples.

DETAILED DESCRIPTION OF PREFERRED EMBODIMENTS

The following examples illustrate but do not limit the present invention. Examples 1,2,17,19 and 20, refer to the preparation of a product (A) according to the invention, while the remaining examples refer to the preparation of the compositions based on the self-extinguishing polymeric compositions and to the inflammability tests relative thereto.

All the parts are by weight unless otherwise stated.

EXAMPLE 1

Preparation of a self-extinguishing product (A), obtained by the reaction in an aqueous medium of melamine and acetic anhydride in equimolecular amounts 189.2 parts of melamine and 153.1 parts of acetic anhydride are suspended in 1500 parts of water in a suitable reactor provided with a stirrer; the suspension is heated to 175° C. in a nitrogen atmosphere. The heating is continued for 20 hours at the said temperature; the pressure rises to 8-9 atmospheres. The product is filtered and is washed twice with 2000 parts of water heated to 90° C., whereby 113 parts of a white product (A) are obtained.

On the product (A) thus obtained, the following determinations are carried out:

Melting Point, above 320° C.;
Solubility in water 0.4 gr/lt at 20° C.;
Elemental analysis: C=27.4%, H=3.5%, N=49.1%;
Equivalent weight determined by titration with sodium hydroxide 156.5;
Equivalent weight determined by titration with perchloric acid in acetic acid 132.2.

The infrared spectrum shows main absorptions at 3470 cm$^{-1}$, 2720-2690 cm$^{-1}$, 1720 cm$^{-1}$, 1630 cm$^{-1}$, 1515 cm$^{-1}$, 1190 cm$^{-1}$, 980 cm$^{-1}$, 785 cm$^{-1}$, 540 cm$^{-1}$, 440 cm$^{-1}$.

EXAMPLE 2

Preparation of a modified self-extinguishing product (A), obtained by the reaction in an aqueous medium of melamine and acetic anhydride in equimolecular amounts in the presence of caprolactam 189.2 parts of melamine, 153.1 parts of acetic anhydride, 12.73 parts of caprolactam and 1500 parts of water are added to one another in the reactor used in Example 1.

The operations are carried out in the same way as in the preceding Example. 117 parts of modified product (A) are obtained after washing.

The following determinations are carried out on the modified product (A):

Melting Point, above 320° C.;
Solubility in water, 0.28 gr/lt at 20° C.;
Elemental analysis: C=28.3%, H=3.5%, N=49.0%;
Equivalent weight determined with sodium hyroxide, 123.3;
Equivalent weight determined by titration with perchloric acid in acetic acid, 133.9.

The infrared spectrum shows main absorptions at 3460 cm$^{-1}$, 2720-2690 cm$^{-1}$, 1730 cm$^{-1}$, 1660 cm$^{-1}$, 1440 cm$^{-1}$, 1190 cm$^{-1}$, 980 cm$^{-1}$, 790 cm$^{-1}$, 540 cm$^{-1}$, 440 cm$^{-1}$.

EXAMPLE 3

Moulding of self-extinguishing polyamide-6 (polycapronamide) and inflammability test relative thereto 6 parts of product (A) modified, obtained according to Example 2, were mixed and extruded in a Creusot-Loire extruder with 94 parts of polyamide-6 (relative viscosity 2.67, measured at 20° C. at a concentration of 1 gr/100 cm$^3$ of 96% sulphuric acid) at 255° C. The polymer containing the additive was moulded in a Negri and Bossi extruding machine (type V 7-9 F.A.) under the following conditions: pressure 100 Kg/cm$^2$, duration of the injection 2 seconds, temperature of the moulds 20° C.; the pieces obtained from the moulding are subjected to test U.L. 94.

The pieces with thicknesses ¼, ⅛, and 1/16 of an inch are classed in class SE-O. Such a classification means that the pieces are self-extinguishing and do not dribble.

EXAMPLE 4

Preparation and spinning-stretching of a composition based on self-extinguishing polyamide-6 (polycapronamide) and inflammability test relative thereto 6.3 parts of modified product (A) (obtained according to Example 2) and 93.6 parts of granules of polyamide-6 (relative viscosity 2.67, measured as in the preceding Example) were extruded in a Creusot-Loire extruder. The temperature of the extruder head is 245° C.

The polymer containing the additive (relative viscosity 2.56) is spun to a count of 40/10 den. under the following conditions:

spinneret temperature: 265° C.;
draw ratio: 3.08.

The fibre has a tenacity of 3.4 gr/den and an elongation of 31.6%. A twine 50 cm long, composed of 300 monofilaments, has been obtained from said yarn; this is subjected to an empirical but significant test to evaluate the self-extinguishing effect. The test consists in determining the number of ignitions necessary for the complete combustion of the twine.

An average of 23 ignitions is required for the sample containing the self-extinguishing additive, whereas an identical twine made from polyamide-6 without any additive requires an average of 4 ignitions to burn completely.

EXAMPLE 5

Spinning and bulking of the self-extinguishing polyamide-6 (polycapronamide) yarn and inflammability test carried out on a carpet made from said yarn 7.1 parts of product (A) obtained according to Example 1 and 92.9 parts of polyamide-6 (relative viscosity 2.67) were extruded in a Creusot-Loire extruder.

The polymer containing the additive, thus obtained, (relative viscosity 2.52), is continuously spun to a count of 15 denier per filament (the temperature of the head is 257° C.). The yarn is then stretched and bulked; then a "loop" type carpet is made from said yarn on a primary foundation of polypropylene non-woven fabric.

The sample carpet is subjected to the test ISO-TC 92 DOC 382, in which it is classed in class 1.

A similar carpet, which however has been obtained using normal polyamide-6, is classified in class 2 according to the same test, viz. its behaviour to the flame is inferior.

EXAMPLE 6

Preparation of a self-extinguishing composition based on polyamide-6,6 (hexamethylenediamine polyadipate) and inflammability test relative thereto 8 parts of modified self-extinguishing product (A) (obtained according to Example 2) and 92 parts of polyamide-6,6 (relative viscosity 2.70) are melted at 290° C. under a nitrogen stream in a glass container provided with a stirrer.

The polymer containing the additive was spun and a 50 cm long twine was prepared from 7 monofilaments.

The test consists in determining the number of ignitions necessary for the complete combustion of the twine. The aforesaid twine required on the average 21 ignitions, whereas a similar twine made from polyamide-6,6 without the additive has required 2 ignitions on the average to burn completely.

EXAMPLES 7-8

Treatment of a cellulosic fabric with a self-extinguishing composition containing the product (A) obtained according to Example 1

19.5 parts of said product (A), finely comminuted (particle size: 1-5 microns) was suspended in a solution containing 6.5 parts of trimethylolmelamine (TMM), 1.6 parts of polyethylene glycol having molecular weight 800 (PEG-800), 0.065 parts of zinc chloride and 0.015 parts of an emulsifier in 72 parts of water acidified to pH 2.5 with phosphoric acid.

A fabric of cellulosic fibre sold under the trademark "Koplon" of the Snia Viscosa Company, having a weight of 130 gr/m$^2$, was treated by immersion into the suspension having the aforesaid composition.

After drying, a weight increase of 25.7% was noted. The oxygen index (L.O.I.) of the product thus treated is 29.2% whereas a sample of the same cellulosic fabric treated with the same finishing composition not containing however the product (A) exhibited an oxygen index of 19%.

A second sample of "Koplon" fabric treated in the same way and with the same finishing suspension containing product (A), is kept in an air oven at 160° C. for 4 minutes. After drying to constant weight, the weight increase was found to be 30.6%; the oxygen index (L.O.I.) is 31.9%.

EXAMPLES 9-10

Treatment of cellulosic fabrics with a self-extinguishing composition, followed by exposure to an ammonia stream A sample of a fabric of "Koplon" (Snia Viscosa) cellulosic fibre is treated in the same way as described in Example 7 and with the same self-extinguishing finishing composition in aqueous suspension, indicated in Example 7.

After said treatment, the sample, placed in a suitable vessel, is homogeneously contacted by a stream of ammonia gas at 70° C. for 60 minutes. After degasifying, the fabric is dried in an oven for 12 hours at 105° C. under a partial vacuum. The weight increase has been calculated to be 31%, the oxygen index (L.O.I.) is 32%.

The same fabric sample treated for 45 minutes with water at 60° C. and with an aqueous solution of sodium bicarbonate at 0.5%, loses 6% of the additive. Therefore the increase in self-extinguishing composition with respect to the initial weight has been 26%; the corresponding oxygen index is 27%.

The Example just described is repeated on a cotton fabric (weight 91 gr/m$^2$); the weight increase was 23% and the oxygen index (L.O.I.) 28.1%. The same fabric of untreated cotton has an L.O.I. of 18.5%.

EXAMPLES 11-12

Treatment of cellulosic fabrics with a self-extinguishing finishing composition containing, besides product (A), also a phosphorus derivative (V)

The self-extinguishing composition comprises 13.8 parts of product (A) of Example 1, 4.6 parts of TMM (trimethylolmelamine), 7.9 parts of sodium polyphosphate, 1.2 parts of PEG-800, 0.05 parts of zinc chloride and 0.011 parts of emulsifier in 72 parts of water. A sample of "Koplon" fabric treated with the said composition, after being kept at 160° C. for 4 minutes and after successive drying at 105° C. under a partial vacuum, shows a weight increase of 28.3%; the oxygen index (L.O.I.) is 35%. Five test samples derived from said fabric sample pass the standard set by DOC FF 3-71. A sample of the same fabric analogously treated with the same finishing composition except that it does not contain product (A), has an oxygen index of 21%. Test pieces derived from this sample do not pass the standard set by DOC FF 3-71.

Similarly, a cotton sample, also treated with the said self-extinguishing composition containing product (A), shows a weight increase of 31% and the oxygen index is 32.7%. In this case too the standard set by test DOC FF 3-71 is passed.

EXAMPLES 13-14

Treatment of polyester fabric, also mixed with cellulosic fibre, with self-extinguishing composition A fabric made from polyester fibre is treated with the same self-extinguishing composition and in the same way as indicated in Example 7.

After drying, the weight increase was 26.8% and the oxygen index is 29.7%. A sample of the same fabric treated with the same finishing composition except that it does not contain the product (A) had an oxygen index of 23%.

A fabric obtained from a mixture comprising 65 parts of polyester fibre and 35 parts of "Koplon", was subjected to the same treatment with the self-extinguishing composition containing product (A), indicated in Example 7. After drying, the weight increase was 29.8%; the oxygen index was 31.1%.

A sample of the same fabric treated with the same composition except that it does not contain product (A), has an oxygen index of 22%.

EXAMPLES 15 and 16

Product (A) synthesized from melamine in the presence of organic acid (butyric anhydride and acetic acid)

The operations are carried out as in Example 1, in the presence of 168.2 parts of melamine, 40 parts of acetic acid, and 106 parts of butyric anhydride in 1000 parts of water.

The product (A) is found to be identical as to its characteristics, to those previously analyzed, as to melting point, solubility in water, titration with perchloric acid, and infrared absorption spectrum.

A twine prepared from yarn containing the aforesaid product (A) as additive, exhibits an identical behaviour as to combustion: 17 ignitions are required.

EXAMPLES 17 and 18

Product (A) synthesized from melamine in the presence of propionic anhydride

The operations are carried out as in Example 1, using 168.2 parts of melamine, 175 parts of propionic anhydride, and 1000 parts of water.

The product (A) thus obtained has identical characteristics to those previously analyzed, as to its melting point, solubility in water, titration with perchloric acid and infrared absorption spectra.

A twine prepared from yarn containing the aforesaid product (A) as additive, exhibits an identical behaviour as to its combustion: 17 ignitions are required.

EXAMPLE 19

Preparation of a product (A) by reaction between melamine and phthalic anhydride in molar ratio 2:1 in an aqueous medium 189.1 gr of melamine (1.5 mols), 111.1 gr of phthalic anhydride (0.75 mols) and, subsequently, 1300 cm$^3$ of water are loaded into a 2 lt autoclave provided with a stirrer. The autoclave is closed and is heated up to 160° C. in an oxygen free nitrogen atmosphere. The heating is continued for 20 hours at the said temperature, under stirring; the autogenous pressure rises to 6–7 atmospheres. The suspension obtained is cooled to room temperature and is filtered, separating the solid part from the mother liquors. The solid is repeatedly washed with water heated to 80°–90° C.; the residue of said washings is 104 gr (product A). From the concentrated wash waters 42.1 gr of phthalic acid are obtained.

The said product (A) has the following characteristics:

Melting point above 320° C.;
Elemental analysis: C=38.3%, H=3.8%, N=52.2%;
Equivalent weight determined by titration with KOH, 316.

The infrared spectrum shows main absorptions at 3350 cm$^{-1}$, 2700–2100 cm$^{-1}$, 1730 cm$^{-1}$, 1440 cm$^{-1}$, 1190 cm$^{-1}$, 790 cm$^{-1}$, 550 cm$^{-1}$.

EXAMPLE 20

Preparation of a product (A) by reaction between melamine and phthalic anhydride in molar ratio 1:1 in an aqueous medium (a) 252.3 gr of melamine (2 mols), 296.2 gr of phthalic anhydride (2 mols) with 1500 cm$^3$ of water are loaded into the apparatus described in Example 19. The same operations as described in Example 19 are carried out. The reaction is continued for 18 hours at 160° C. After cooling, the solid is separated from the water; the residue is washed repeatedly with hot water and extracted with methyl alcohol under reflux.

The residue of the extractions (product A) is in the amount of 369.6 gr. After uniting the mother liquors with the wash waters, 155.2 gr of phthalic acid and 124.4 gr of phthalic anhydride are recovered by concentration.

The said product (A) has the following characteristics:

Melting point above 320° C.
Solubility in water at 100° C., 0.07%;
Elemental analysis: C=41.1%, H=4.0%, N=44.7%;
Equivalent weight determined by titration with KOH, 214.

The infrared spectrum shows main absorptions at 3350 cm$^{-1}$, 2700–2100 cm$^{-1}$, 1730 cm$^{-1}$, 1440 cm$^{-1}$, 1190 cm$^{-1}$, 990 cm$^{-1}$, 780 cm$^{-1}$, 630–660 cm$^{-1}$, 540 cm$^{-1}$.

(b) When the reaction between melamine and phthalic anhydride in equimolecular ratio was prolonged for 30 hours at 160° C., 368.4 gr of product (A) were obtained after extraction with hot water and 194.8 gr of phthalic acid are recovered.

This product (A) has a melting point above 320° C., equivalent weight 215, and the following elemental analysis: C=42.0%, H=4.5%, N=46.5%.

EXAMPLE 21

Preparation and spinning of self-extinguishing polyamide-6 (polycapronamide) and inflammability test relative thereto 12.15 Kg of polyamide-6 chips (relative viscosity 3.2, measured in 96% sulphuric acid at a concentration of 1% and at 20° C.) together with 780 gr of a mixtures of products (A) obtained according to Examples (20a) and (20b), in equal parts by weight (6.4% by weight with respect to the polyamide-6), 39 gr of diphenylcarbonate and 13 gr of titanium dioxide are extruded in a Creusot-Loire extruder. The temperature of the extruder head is 245° C.

1 Kg. of polyamide-6 chips containing the self-extinguishing additive, thus prepared, is spun to a count 40/10 (40 den, 10 filaments) under the following conditions:

Temperature of the spinning heads 231° C.;
Take-up speed 680 mt/min;
Draw ratio 3.52;
Temperature of the first cylinder 85° C.

The fibre thus obtained has a tenacity of 2.86 gr/den, and an elongation of 378%. The relative viscosity of the yarn, measured as hereinbefore described, is 2.0. Fifteen samples of stockings obtained from said yarn (weight 100 gr/m$^2$) were subjected to the test DOC FF 3-71. All of the samples passed the required standard (on each test, three glass filaments are interwoven). Under the same conditions, the same polyamide without the additive did not pass the test.

EXAMPLE 22

Preparation of a moulding mass from self-extinguishing polyamide-6 (polycapronamide) and inflammability test relative thereto 1 Kg of polyamide-6 chips containing 3.2% of flame-retardant product (A) as described in Example 19, are moulded in an extruding machine Negri and Bossi (type V 7-9 F.A.) under the following conditions: pressure about 100 Kg/cm$^2$; duration of the injection 1 second, temperature of the moulds 80° C.

Samples having thickness of ¼, ⅛, and 1/16 of an inch, five for each thickness, are subjected to the U.L. test. The combustion lengths are 0.8, 0.7 and 0.2 cm respectively for the three thicknesses. All the samples are classed in class SE-O.

EXAMPLE 23

Preparation of a self-extinguishing composition based on polyamide-6,6 (hexamethylenediamine polyadipate) and inflammability test relative thereto 48.5 gr of polyamide-6,6 (relative viscosity 2.65) are melted together with 1.5 gr (3.1%) of the product (A) obtained according to Example 19, at 290° C. in a glass container provided with a stirrer, under nitrogen stream (O$_2$ less than 10 ppm). After complete melting, the mass is stirred in a nitrogen stream for 10 minutes.

The polymer containing the additive has a relative viscosity of 2.1. A twine of 7 monofilaments obtained from this product required 22 ignitions to burn completely whereas a comparable twine from the same polyamide but not containing the additive, required only 2 ignitions.

We claim:

1. A self-extinguishing polymeric composition which comprises a polymer selected from the group consisting of polyamides, copolyamides, polyesters, copolyesters, regenerated cellulose, cotton and mixtures thereof and a self-extinguishing additive product (A) prepared by reacting, in the presence of water, and at a temperature from 100° to 300° C., melamine and at lease one acidic compound, said acidic compound being an anhydride selected from the group consisting of acetic, propionic, butyric, phthalic anhydrides, and mixtures thereof; an acid selected from the group consisting of formic, acetic, propionic, butyric acids, and mixtures thereof; or mixtures thereof, said additive product (A) having a nitrogen content of 3 to 60% by weight and a melting point of at least 300° C.

2. The composition of claim 1 wherein said acidic compound is an anhydride selected from the group consisting of acetic anhydride, propionic anhydride, butyric anhydride, phthalic anhydride and mixtures thereof.

3. The composition of claim 1 wherein the acidic compound is selected from the group consisting of formic acid, acetic acid, propionic acid, butyric acid, and mixtures thereof.

4. A self-extinguishing polymeric composition which comprises a polyamide polymer and a self-extinguishing additive product (A) having a nitrogen content of 3 to 60% by weight and a melting point of at least 300° C. and being prepared by reacting, in the presence of caprolactam and water, and at a temperature from 100° to about 300° C., a sufficient amount of melamine with at least one acidic compound selected from the group consisting of carboxylic acids, carboxylic acid anhydrides and mixtures thereof, to provide caprolactam with additive product (A) present at from 0.5 to 30% by weight of the caprolactam.

5. The composition of claim 4, wherein said acidic compound is acetic anhydride.

6. A self-extinguishing additive composition (A) having a nitrogen content of 3–60% by weight and a melting point of at least 300° C. and being prepared by reacting in the presence of caprolactam and water, and at a temperature from about 100° to 300° C., a sufficient amount of melamine with an acidic compound selected from the group consisting of organic acids and anhydrides of organic acids, to provide caprolactam with additive composition (A) present at from 0.5 to 30% by weight.

* * * * *